United States Patent [19]

Cushman et al.

[11] Patent Number: 4,945,075

[45] Date of Patent: Jul. 31, 1990

[54] OXIDATIVE SECONDARY RHODIUM RECOVERY PROCESS

[75] Inventors: Michael R. Cushman; Vincent A. Nicely; Brent A. Tennant; Joseph R. Zoeller, all of Kingsport, Tenn.

[73] Assignee: Eastman Kodak Company, Rochester, N.Y.

[21] Appl. No.: 445,253

[22] Filed: Dec. 4, 1989

[51] Int. Cl.$^5$ .............. B01J 38/68; B01J 38/54; C01G 55/00; C07C 51/10
[52] U.S. Cl. ........................... 502/24; 423/22; 502/28; 502/32; 562/607; 562/891
[58] Field of Search ............... 502/24, 28, 32; 423/22; 260/549; 562/607

[56] References Cited

U.S. PATENT DOCUMENTS

| | | | |
|---|---|---|---|
| 4,388,217 | 6/1983 | Hembre et al. | 502/28 |
| 4,434,240 | 2/1984 | Pogach | 502/24 |
| 4,578,368 | 3/1986 | Zoeller | 502/28 |
| 4,650,649 | 3/1987 | Zoeller | 423/22 |

*Primary Examiner*—Paul E. Konopka
*Attorney, Agent, or Firm*—J. Frederick Thomsen; William P. Heath, Jr.

[57] ABSTRACT

Disclosed is a process for recovering rhodium catalyst values from "tars" formed during the preparation of acetic anhydride by the rhodium catalyzed carbonylation of a mixture of methyl iodide and methyl acetate and/or dimethyl ether. The disclosed process provides a means for the recovery of rhodium values which normally are not extracted from the tars by treating a methyl iodide solution of such tars with certain oxidants.

6 Claims, No Drawings

OXIDATIVE SECONDARY RHODIUM RECOVERY PROCESS

This invention pertains to a process for recovering rhodium catalyst values from "tars" formed during the preparation of acetic anhydride by the rhodium catalyzed carbonylation of a mixture of methyl iodide and methyl acetate and/or dimethyl ether. More specifically, this invention pertains to an oxidative process for the recovery of rhodium values which normally are not extractable from the tars.

The use of catalyst systems comprising rhodium and an iodine compound in the preparation of acetic anhydride by the carbonylation of methyl acetate has been reported extensively in the patent literature. See, for example, U.S. Pat. Nos. 3,927,078, 4,046,807, 4,374,070 and 4,559,183 and European Pat. Nos. 8396 and 87,870. These patents disclose that the reaction rate can be increased if the catalyst system includes a promoter such as certain amines, quaternary ammonium compounds, phosphines and inorganic compounds such as lithium compounds.

The formation of tar in carbonylation acetic anhydride processes and the problem of recovering catalyst value therefrom are described in U.S. Pat. No. 4,388,217 and European Pat. No. 255,389. Several processes have been described in the literature for the separation of rhodium from these tars. The majority of these recovery processes involve cumbersome precipitations of the rhodium-containing species and co-catalysts using a variety of organic solvents and an optional subsequent dissolution of the ionic iodide promoters with water. Enriched rhodium-containing material is either returned to the reactor or ashed for the rhodium value. See U.S. Pat. Nos. 4,442,304, 4,440,570, 4,556,644, 4,629,711, 4,746,640, 4,605,541, 4,659,682, and 4,434,240. A simpler variant involving solvent removal, aqueous extraction and ashing is described in U.S. Pat. No. 4,434,241.

U.S. Pat. No. 4,434,240 discloses the use of reagents such as alkali metal hydroxides, hydrogen peroxide or its alkali metal salts, and reducing agents, such as sodium borohydride, formaldehyde, and sodium bisulfite to aid in precipitation. The peroxide used in accordance with the disclosed process apparently is consumed in oxidizing iodide ion to elemental iodine.

The handling and transfer of fine, rhodium-containing solids are cumbersome on a commercial scale and liquid phase processes for recovering rhodium catalyst values therefore are preferable in most industrial operations. Several such processes have been described. European Patent Application No. 250,103 describes a liquid phase electrochemical separation.

A particularly useful liquid phase process for recovering catalyst values is described in U.S. Pat. No. 4,388,217 wherein a catalyst-tar solution is submitted to an extraction using methyl iodide and aqueous hydrogen iodide. In the practice of the extraction process, a substantial amount of the rhodium present in the rhodium-tar solution is recovered in the aqueous hydrogen iodide phase which may be recycled to the carbonylation process. The presence of the hydrogen iodide in the aqueous phase stabilizes the water-soluble rhodium compound or compounds, thereby preventing the loss of insoluble rhodium which can plate out on the extraction equipment and/or the walls of pipes, vessels, etc. Most of the tar component of the catalyst-tar solution is recovered in the methyl iodide phase.

The above described extraction process generally is very efficient, leaving only small quantities of rhodium behind in an unextractable form. Since rhodium is extremely expensive, this small portion of rhodium must also be recovered or the acetic anhydride manufacturing process will be subjected to very high catalyst replacement costs. The ashing and recycling involved in recovering these small quantities of rhodium still represents an economic burden on the carbonylation-based production of acetic anhydride. Three approaches to recovering the remaining rhodium and iodine present in the tar are described in the patent literature. Two similar processes which involve the precipitation of rhodium in acetic acid are described in U.S. Pat. Nos. 4,578,368 and 4,650,649. These processes suffer the same drawbacks associated with prior precipitation-based processes with the exception that the scale is significantly reduced. A more useful extractive process using aqueous ammonia is described in U.S. Pat. No. 4,364,907. This ammonia-based process requires the removal of significant quantities of aqueous ammonia from the rhodium-containing solution. The process also introduces small quantities of ammonia into the system which can adversely affect the carbonylation process due to the formation of insoluble tetramethyl ammonium salts.

The process provided by this invention involves a secondary, liquid-phase treatment of the tars containing rhodium catalyst values, resulting from the above-described methyl iodide/aqueous hydrogen iodide extraction process, with oxidants such as peracetic acid, hydrogen peroxide and ozone. We have discovered that oxidation of the methyl iodide solution of tars containing rhodium not extracted by the primary methyl iodide/aqueous hydrogen iodide extraction process permits the recovery of previously unextracted rhodium from the tars using a subsequent extraction with aqueous hydrogen iodide. Our novel process is completely compatible with the extraction and carbonylation processes described hereinabove since it does not result in the introduction of any extraneous material to the overall production system. The process is essentially free of solids and is amenable to continuous operation, especially in conjunction with the described methyl iodide/aqueous hydrogen iodide extraction process.

The process of this invention therefore comprises the recovery of rhodium catalyst values from a catalyst-tar solution derived from a production system in which acetic anhydride is prepared by contacting a mixture of methyl acetate and/or dimethyl ether and methyl iodide with carbon monoxide in the presence of a rhodium catalyst comprising the steps of:

1. submitting the catalyst-tar solution to an extraction with a combination of methyl iodide and aqueous hydrogen iodide and recovering (a) the aqueous phase containing most of the rhodium catalyst values, and (b) the methyl iodide phase containing most of the tar which contains minor amounts of the rhodium catalyst values;
2. treating the methyl iodide phase of step 1 with an oxidant selected from peracetic acid, hydrogen peroxide and ozone; and
3. submitting the treated methyl iodide phase of step 2 to an extraction with aqueous hydrogen iodide to recover in the aqueous phase rhodium catalyst values present in the treated methyl iodide phase.

The production system from which the catalyst-tar solution referred to above is derived includes systems in which essentially all of the product is acetic anhydride or in which both acetic anhydride and acetic acid are produced in varying ratios. Thus, the mixture fed to the carbonylation reactor may include methanol and/or water in addition to methyl acetate and/or dimethyl ether and methyl iodide.

The amount of the oxidant required must exceed the amount which converts the iodide ion ($I^-$) present in the methyl iodide solution of tar to elemental iodine ($I_2$). When all of the iodide ion has been converted to elemental iodine, the oxidative liberation of the previously unextracted rhodium values proceeds quickly and additional oxidant is only marginally effective beyond this point. In practice, good results have been achieved by the use of about 0.08 and 0.15 moles of oxidant per liter of tar solution. However, since extraction efficiency of the initial extraction (step 1 above) can vary significantly in commercial operations, the optimum amount of oxidant required also will vary. Accordingly, the optimum amount required may be determined empirically from time to time by the operator of the process.

Although we have demonstrated that several oxidants are useful in the process of this invention, the preferred oxidant, based upon reaction rate and process compatibility, is peracetic acid. It is well-known to those skilled in the art that peracetic acid may be generated in situ by several processes, the most important of which comprise the dissolution of hydrogen peroxide in acetic acid or acetic anhydride and the interaction of oxygen with acetaldehyde. These methods of in situ generation of the oxidant are within the scope of our invention. A particularly useful source of peracetic acid is the epoxidation process described by J. T. Lutz, Jr. in Kirk-Othmer, Encyclopedia of Chemical Technology, 3rd Ed., Vol. 9, p. 225–258 (1980). In the epoxidation process, peracetic acid is generated by contacting acetic acid with hydrogen peroxide in the presence of an acidic ion exchange resin.

The temperatures at which the oxidation (step 2) may be carried out preferably are between about 0° C. and 43° C. (the boiling point of methyl iodide). Higher temperatures, e.g., up to about 175° C., may be used if the process is carried out at super-atmospheric pressure. Temperatures of less than 0° C., e.g., as low as −25° C., may be used but such low temperatures may result in the precipitation of active peroxides which represent a serious safety hazard.

The step 2 oxidation may be carried out in any suitable vessel using agitation sufficient to provide intimate contact between the oxidant and the methyl iodide/tar solution. For example, when using peracetic acid or hydrogen peroxide, a stirred reactor may be used. When ozone is used, it may be fed to a gas sparger at or near the bottom of a columnar or tower reactor. In a preferred mode of operation, the aqueous hydrogen iodide phase recovered from step 3 is fed to the extraction system of step 1, e.g., the extraction process described in U.S. Pat. No. 4,388,217.

Our novel process is further illustrated by the following examples wherein the extraction efficiency, i.e., the percentage of rhodium (calculated as [Rh] by atomic absorption analyses) extracted into the aqueous hydrogen iodide phase, is determined by the formula:

$$\frac{Rh_{HI}}{Rh_{HI} + Rh_{MeI}} \times 100$$

wherein $Rh_{HI}$=weight [Rh] in the aqueous hydrogen iodide (HI) phase; and $Rh_{MeI}$=weight [Rh] in the methyl iodide (MeI) phase.

EXAMPLES 1–7

Varying amounts of peracetic acid or hydrogen peroxide were added to samples (50 mL) of tar-methyl iodide mixtures obtained from the extraction process described in U.S. Pat. No. 4,388,217 in a 100 mL, round-bottom flask and the resulting mixtures were stirred at ambient temperature for different periods of time. At the end of the oxidant treatment time, each mixture was shaken thoroughly in a 125 mL separatory funnel with 50 mL of 35% aqueous hydrogen iodide. The aqueous and organic phases were allowed to separate and each was analyzed for rhodium.

The results obtained are shown in Table I which sets forth the oxidant (PAA=peracetic acid; HP=hydrogen peroxide) and the amount thereof (mL) used and the period of time (Time, hours) the oxidant and tar-methyl iodide mixture was stirred in each example prior to the aqueous hydrogen iodide extraction. The [Rh]-HI Phase and [Rh]-MeI Phase refer to the amount (ppm) rhodium found in the aqueous hydrogen iodide and methyl iodide phases, respectively.

Comparative Examples C-1 and C-2 show the results achieved when 50 mL samples of the same tar-methyl iodide mixtures used in Examples 1 and 2 are extracted as described without the oxidative treatment of this invention.

TABLE I

| Example | Oxidant/ Amount | Time | [Rh]-HI Phase | [Rh]-MeI Phase | Extraction Efficiency |
|---|---|---|---|---|---|
| 1 | PAA-2.0 | 0.5 | 24 | 2 | 88% |
| C-1 | — | — | 7 | 16 | 21% |
| 2 | PAA-2.0 | 0.5 | 30 | 6 | 76% |
| C-2 | — | — | 16 | 31 | 24% |
| 3 | PAA-3.0 | 0.5 | 30 | 6 | 76% |
| 4 | PAA-1.0 | 0.5 | 21 | 22 | 37% |
| 5 | PAA-2.0 | 1.0 | 32 | 7 | 74% |
| 6 | PAA-2.0 | 2.0 | 30 | 6 | 76% |
| 7 | HP-1.0 | 0.5 | 22 | 25 | 35% |

EXAMPLE 8

A 3-necked, 250 mL, round-bottom flask equipped with a magnetic stirrer bar and a reflux condenser was connected to a commercial ozone generator and the third neck was sealed with a stopper. The flask was charged with 150 mL of pre-extracted tar-methyl iodide mixture (described in the preceding examples) and chilled to 0° C. A stream of 7.1% ozone in oxygen was fed to the stirred mixture at a rate of 5 standard cubic feet per hour for 15 minutes. The ozone feed was discontinued and the mixture was purged with oxygen for 5 minutes to remove residual ozone. A considerable amount of the methyl iodide was lost during the purge and the volume of the mixture was reduced significantly. The mixture was then transferred to a 500 mL separatory funnel and extracted with 150 mL (195.5 g) of 35% aqueous hydrogen iodide. The methyl iodide phase (241.7 g) and aqueous hydrogen iodide phase (196.3 g) were separated and analyzed for rhodium. The results obtained were:

| [Rh]-HI Phase | 14 ppm |
|---|---|
| [Rh]-MeI Phase | 15 ppm |
| Extraction Efficiency | 43% |

Extraction of a 150 mL sample of the same pre-extracted tar-methyl iodide mixture with aqueous hydrogen iodide as described in Example 8 gave an extraction efficiency of 21%.

EXAMPLE 9

A sample of the tar-containing methyl iodide mixture obtained from the extraction process described in U.S. Pat. No. 4,388,217 was carefully analyzed for rhodium content and found to contain 20 ppm rhodium. A sample (105 g, 50 mL, 2.1 mg Rh) of this mixture was stirred with 2.0 mL of 28% peracetic acid for 30 minutes at room temperature. The reaction mixture then was transferred to a separatory funnel containing 66 g (50 mL) of 35% aqueous hydrogen iodide. The layers were shaken and subsequently separated to give an aqueous hydrogen iodide layer and a methyl iodide layer. Both were carefully weighed and analyzed for rhodium content:

| [Rh]-HI Phase | 24 ppm | (1.65 mg Rh) |
|---|---|---|
| [Rh]-MeI Phase | 2 ppm | (0.21 mg Rh) |

The amounts of rhodium found in the HI and MeI phases represent 79% and 10%, respectively, of the rhodium content of the initial tar-containing methyl iodide mixture used.

All the equipment used throughout this experiment was retained and washed with small quantities of acetone to ascertain the amount of rhodium remaining in the equipment. The amount of rhodium thus found was 0.10 mg representing 5% of the rhodium content of the initial tar-containing methyl iodide mixture used. This gives an rhodium accountability of 94% for the experiment.

The invention has been described in detail with particular reference to preferred embodiments thereof, but it will be understood that variations and modifications may be effected within the spirit and scope of the invention.

We claim:

1. Process for the recovery of rhodium catalyst values from a catalyst-tar solution derived from a production system in which acetic anhydride is prepared by contacting a mixture of methyl acetate and/or dimethyl ether and methyl iodide with carbon monoxide in the presence of a rhodium catalyst comprising the steps of:
   1. submitting the catalyst-tar solution to an extraction with a combination of methyl iodide and aqueous hydrogen iodide and recovering (a) the aqueous phase containing most of the rhodium catalyst values, and (b) the methyl iodide phase containing most of the tar which contains minor amounts of the rhodium catalyst values;
   2. treating the methyl iodide phase of step 1 with an oxidant selected from peracetic acid, hydrogen peroxide and ozone; and
   3. submitting the treated methyl iodide phase of step 2 to an extraction with aqueous hydrogen iodide to recover in the aqueous phase rhodium catalyst values present in the treated methyl iodide phase.

2. Process according to claim 1 wherein the oxidant of step 2 is peracetic acid.

3. Process according to claim 1 wherein step 2 comprises treating the methyl iodide phase of step 1 with peracetic acid at a temperature of about 0° to 43° C.

4. Process according to claim 1 wherein the catalyst-tar solution is derived from a production system in which acetic anhydride and acetic acid are prepared by contacting a mixture of methyl acetate and/or dimethyl ether, methyl iodide, methanol and/or water with carbon monoxide.

5. Process for the recovery of rhodium catalyst values from a catalyst-tar solution derived from a production system in which acetic anhydride is prepared by contacting a mixture of methyl acetate and/or dimethyl ether and methyl iodide with carbon monoxide in the presence of a rhodium catalyst comprising the steps of:
   1. submitting the catalyst-tar solution to an extraction with a combination of methyl iodide and aqueous hydrogen iodide and recovering (a) the aqueous phase containing most of the rhodium catalyst values, and (b) the methyl iodide phase containing most of the tar which contains minor amounts of the rhodium catalyst values;
   2. treating the methyl iodide phase of step 1 with peracetic acid;
   3. submitting the treated methyl iodide phase of step 2 to an extraction with aqueous hydrogen iodide to recover in the aqueous phase rhodium catalyst values present in the treated methyl iodide phase; and
   4. feeding the aqueous phase of step 3 to the extraction system of step 1.

6. Process according to claim 5 wherein the catalyst-tar solution is derived from a production system in which acetic anhydride and acetic acid are prepared by contacting a mixture of methyl acetate and/or dimethyl ether, methyl iodide, methanol and/or water with carbon monoxide.

* * * * *